United States Patent [19]

Anderson et al.

[11] Patent Number: 5,844,041
[45] Date of Patent: Dec. 1, 1998

[54] PROCESS FOR INCREASING THE VISCOSITY OF AQUEOUS SOLUTIONS OF HOMOGENEOUS COPOLYMERS OF VINYL PYRROLIDONE AND N-3, 3-DIMETHYLAMINOPROPYL METHACRYLAMIDE

[75] Inventors: Lowell Ray Anderson, Morristown; Kou-Chang Liu, Wayne, both of N.J.; Hemant Parikh, Harriman, N.Y.

[73] Assignee: ISP Investments Inc., Wilmington, Del.

[21] Appl. No.: 910,127

[22] Filed: Aug. 13, 1997

Related U.S. Application Data

[63] Continuation-in-part of Ser. No. 781,318, Jan. 9, 1997, abandoned.

[51] Int. Cl.$^6$ ..................................................... C08L 37/00
[52] U.S. Cl. ................................................ 524/548
[58] Field of Search ................................. 524/548

[56] References Cited

U.S. PATENT DOCUMENTS 4,223,009  9/1980  Chakrabarti .
4,923,694  5/1990  Shih et al. .
5,045,617  9/1991  Shih et al. .

FOREIGN PATENT DOCUMENTS 3136894  6/1991  Japan .

*Primary Examiner*—Bernard Lipman
*Assistant Examiner*—N. Sarofim
*Attorney, Agent, or Firm*—Walter Katz; William J. Davis; Marilyn J. Maue

[57] ABSTRACT

A process is described for increasing the viscosity and high humidity curl retention of aqueous solutions of homogeneous copolymers of 20–99% vinyl pyrrolidone (VP) and 1–80% N-3,3-dimethylamino-propyl methacrylamide (DMAPMA). The high viscosity solutions are particularly useful as the active component of hair care products.

5 Claims, No Drawings

PROCESS FOR INCREASING THE VISCOSITY OF AQUEOUS SOLUTIONS OF HOMOGENEOUS COPOLYMERS OF VINYL PYRROLIDONE AND N-3, 3-DIMETHYLAMINOPROPYL METHACRYLAMIDE

RELATED PATENT APPLICATION

This application is a continuation-in-part of application Ser. No. 08/781,318, filed Jan. 9, 1997, now abandoned.

BACKGROUND OF THE INVENTION

1. Field of the Invention

This invention relates to homogeneous copolymers of vinyl pyrrolidone (VP) and N-3,3-dimethylaminopropyl methacrylamide (DMAPMA), and, more particularly, to a process for making aqueous solutions of such copolymers which have high viscosity properties.

2. Description of the Prior Art

Kou-Chang Liu et al., in copending U.S. patent application Ser. No. 08/365,258, filed Dec. 28, 1994, (FDN-2246), described a process for making substantially homogeneous copolymers of VP and DMAPMA of predetermined composition, generally 20–99% by weight, preferably about 80% VP, and 1–80% by weight, preferably about 20% DMAPMA, by copolymerization of the monomers in the presence of an initiator. Completion of the reaction is evidenced by a low residual monomer level. The copolymer product was an aqueous solution of low viscosity, at 5–20% solids with excellent clarity and hold use properties. However, it is sometimes advantageous to provide such aqueous copolymer solutions with an increased viscosity and curl retention than is possible upon completion of the copolymerization. Such increased viscosity aqueous copolymer solutions are useful in hair care products.

Accordingly, the object of this invention is to provide a process for increasing the viscosity of aqueous solutions of homogeneous copolymers of VP and DMAPMA for use in hair care products.

Another object herein is to provide high viscosity aqueous copolymer solutions of VP and DMAPMA which also have advantageous hold and clarity properties.

SUMMARY OF THE INVENTION

A process for making aqueous solutions of substantially homogeneous copolymers of VP and DMAPMA having a compolymer compositional range of 20–99% by weight VP and 1–80% by weight DMAPMA, having advantageously high viscosity levels, which comprises treating the aqueous solution of the copolymer with t-butylperoxy pivalate to increase its viscosity to the desired level.

DETAILED DESCRIPTION OF THE INVENTION

In accordance with the invention, there is provided a process for increasing the viscosity of aqueous solutions of homogeneous copolymers of VP and DMAPMA. The process herein commences upon completion of the copolymerization reaction, which provides an aqueous solution of the copolymer of low viscosity. The solution then is given one or more, preferably several, injections of t-butylperoxy pivalate (Lupersol® 11), suitably at an elevated temperature, and preferably at about 68° to 75° C. The total amount of t-butylperoxy pivalate injected during this treatment generally is up to about 0.1% of the weight of the copolymer solution.

The effect of this treatment is a substantial increase in the viscosity of the aqueous copolymer solution, even reaching a Brookfield viscosity of 200,000 cps at 10% solids, which is 10 times the viscosity of the untreated solution. Preferably, for hair care use, the viscosity level is about 10,000 to 75,000 cps. As a result of this treatment, the hold property of the copolymer solution also is increased, generally by a factor of about 2, as compared to untreated solutions, while the clarity of the solution is still characterized as being haze-free.

The invention will now be described in more detail by reference to the following working examples.

EXAMPLES 1–5

A nitrogen sparged, 2-1 water-jacketed reactor was charged with 1800 g of a neutralized, homogeneous copolymer of VP/DMAPMA, in an 80:20 weight ratio in water at 10.5% solids. The solution then was heated to 68° C.

The copolymer was prepared as disclosed in the above identified patent application. Thereafter one or more injections of Lupersol® 11* initiator was added to the solution every 3 hours. The untreated solution was considered the control. The resultant viscosity of the aqueous copolymer solutions with and without injections of the initiator is given in Table 1 below.

Lupersol® 11 is a 75% solution of t-butylperoxy pivalate in mineral oil.

TABLE 1

| EX. NO. | NO. OF INJECTIONS | TOTAL AMOUNT (ml) | BROOKFIELD VISCOSITY (cps) |
| --- | --- | --- | --- |
| 1 | None | — | 20,800 |
| 2 | 1 | 0.5 | 32,200 |
| 3 | 2 | 0.75 | 48,000 |
| 4 | 2 | 1.0 | 67,000 |
| 5 | 3 | 1.5 | 76,000 |

The results in Table 1 demonstrate that the treated solutions experienced a substantial increase in viscosity, generally up to about 75,000 cps. In one run, however, the viscosity reached 190,000 cps. The hold property also was increased to up to twice the value of an untreated sample. The haze increased somewhat in the treated samples but they still remained relatively clear. The enhanced viscosity and hold properties of such treated solutions thus provided desirable use solutions for hair care products.

While the invention has been described with particular reference to certain embodiments thereof, it will be understood that changes and modifications may be made which are within the skill of the art. Accordingly, it is intended to be bound only by the following claims, in which:

What is claimed is:

1. A process for increasing the viscosity of aqueous solutions of substantially homogeneous copolymers of VP and DMAPMA having a copolymer compositional range of 20–99% by weight VP and 1–80% by weight DMAPMA from about 18,000 cps to up to about 200,000 cps at 10% solids, which comprises heating the aqueous solution of the copolymer with a sufficient amount of t-butylperoxy pivalate to increase its viscosity to the desired level.

2. A process according to claim 1 wherein heating is carried out at about 68°–75° C.

3. A process according to claim 1 wherein the viscosity is increased to a value of about 18,000 to 75,000 cps.

4. A process according to claim 1 wherein t-butylperoxy pivalate is added in several stages or continuously in a total amount up to about 0.1% of the weight of the copolymer solution.

5. A process according to claim 1 wherein the copolymer in the aqueous solution is neutralized before being treated.

* * * * *